United States Patent [19]

Block

[11] 4,093,679

[45] June 6, 1978

[54] HYDROXYALKYL OR AMINOALKYL ESTERS OF PHOSPHOLANE PHOSPHONIC AND PHOSPHINIC ACIDS

[75] Inventor: Hans-Dieter Block, Cologne, Germany

[73] Assignee: Bayer Aktiengesellschaft, Leverkusen, Germany

[21] Appl. No.: 741,576

[22] Filed: Nov. 12, 1976

[30] Foreign Application Priority Data

Nov. 21, 1975 Germany .............................. 2552316

[51] Int. Cl.$^2$ ............................ C07F 9/32; C07F 9/40
[52] U.S. Cl. ............................. 260/927 R; 260/453 R; 260/566 R; 260/978
[58] Field of Search .......................... 260/978, 927 R

[56] References Cited

U.S. PATENT DOCUMENTS 2,372,244  3/1945  Adams et al. ................. 260/978 X
3,725,466  4/1973  Uhing .......................... 260/927 R X Primary Examiner—Richard L. Raymond
Attorney, Agent, or Firm—Burgess, Dinklage & Sprung

[57] ABSTRACT

A hydroxyalkyl or aminoalkyl ester of a phospholane phosphonic or phosphinic acid of the formula

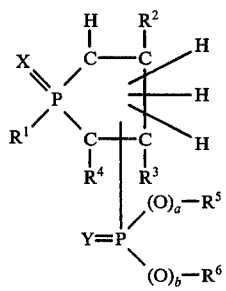

in which
$R^1$ is alkyl with 1 to 10 carbon atoms or aryl with up to 14 carbon atoms,
$R^2$, $R^3$ and $R^4$ each independently is alkyl with 1 to 4 carbon atoms, hydrogen, chlorine or bromine,
$R^5$ and $R^6$ each independently is alkyl with 1 to 8 carbon atoms and, where $a$ or $b$ = 0, also an aryl radical with up to 8 carbon atoms and, where $a$ = 1, also I/m of an m-valent cation or a hydroxy alkylene or imino alkylene radical of the formula

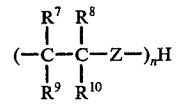

$R^7$ and $R^8$ each independently is hydrogen, optionally substituted alkyl with 1 to 6 carbon atoms, optionally substituted phenyl, alkenyl with 2 to 4 carbon atoms, chloromethyl, bromomethyl, hydroxy methyl or etherified or esterified hydroxy methyl, in addition to which $R^7$ and $R^8$ may together be an alkylene bridge of 2 to 4 carbom atoms to form a ring,
$R^9$ and $R^{10}$ each independently is hydrogen or alkyl with 1 to 2 carbon atoms,
Z is oxygen or imino,
$n$ is a number from 1 to 30,
X and Y each independently is oxygen or sulphur, and
$a$ and $b$ each independently is 0 or 1, with the proviso that at least one of $a$ and $b$ is 1 and at least one of $R^5$ and $R^6$ is one of the above-mentioned hydroxy alkylene or imino alkylene radicals, is produced by reacting a phospholane phosphonic or phospholane phosphinic acid of the formula

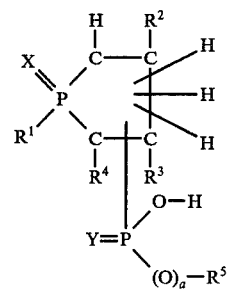

with at least one alkylene oxide or alkylene imine of the formula

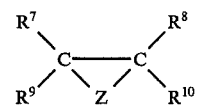

The products are useful for converting isocyanates into carbodiimides.

2 Claims, No Drawings

HYDROXYALKYL OR AMINOALKYL ESTERS OF PHOSPHOLANE PHOSPHONIC AND PHOSPHINIC ACIDS

This invention relates to new phospholane phosphonic acid esters and phospholane phosphinic acid esters corresponding to the general formula

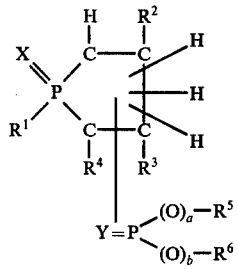 (I)

in which
R¹ represents an alkyl radical with 1 to 10 carbon atoms, preferably with 1 to 2 carbon atoms, or an aryl radical with up to 14 carbon atoms, preferably with 6 – 7 carbon atoms,
R², R³ and R⁴, which may be the same or different, represent an alkyl radical containing 1 to 4 carbon atoms, preferably methyl, hydrogen, chlorine or bromine,
R⁵ and R⁶, which may be the same or different, represent an alkyl radical with 1 to 8 carbon atoms, preferably with 1 to 4 carbon atoms, and where $a$ or $b = 0$, may represent an aryl radical with up to 8 carbon atoms, preferably with 6 carbon atoms, and where $a = 1$ also 1/m of an m-valent cation, such as a metal cation, preferably an alkali metal cation, ammonium, guanidinium, phosphonium or hydrogen or a hydroxy or imino alkylene radical

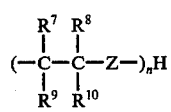

where R⁷ and R⁸, which may be the same or different, represent hydrogen, an optionally substituted alkyl radical containing 1 to 6 carbon atoms, preferably methyl or ethyl, an optionally substituted phenyl radical, an alkenyl radical with 2 to 4 carbon atoms, the chloromethyl radical, the bromomethyl radical, the hydroxy methyl radical or an etherified or esterified hydroxy methyl radical, in addition to which R⁷ and R⁸ may also be attached through an alkylene bridge of 2 to 4 carbon atoms to form a ring,
R⁹ and R¹⁰, which may be the same or different, represent hydrogen or an alkyl radical with 1 – 2 carbon atoms,
Z represents oxygen or an imino group,
n is a number between 1 and 30,
X and Y, which may be the same or different, represent oxygen or sulphur, and
a and b which may be the same or different represent 0 or 1, with the proviso that at least one of the indices $a$ and $b$ has the value 1 and at least one of the substituents R⁵ and
R⁶ represents one of the above-mentioned hydroxy alkylene or imino alkylene radicals.

The present invention also provides a process for producing the above-mentioned phospholane phosphonic and phospholane phosphinic acid esters. This process is characterized by the fact that phospholane phosphonic or phospholane phosphinic acids corresponding to the general formula (III)

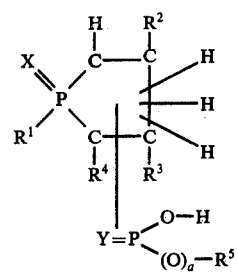 (III)

in which R¹, R², R³, R⁴, R⁵, X, Y and $a$ have the same meanings as in formula I are reacted with alkylene oxides and/or alkylene imines corresponding to the general formula

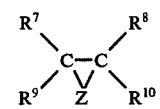 (V)

in which R⁷, R⁸, R⁹, R¹⁰ and Z are as defined in connection with formula (I).

The starting materials (III) used for the process according to the invention are described in application Ser. No. 648,710, filed Jan. 13, 1976, now U.S. Pat. No. 4,052,484, the disclosure of which is incorporated herein by reference. Compounds such as these are obtained by reacting unsaturated 5-membered cyclic phosphine oxides corresponding to the formulae

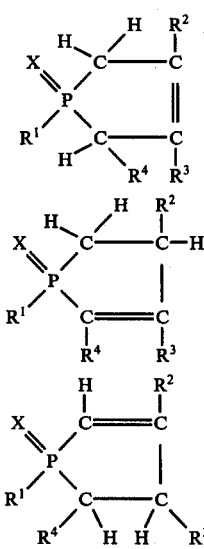

in which R¹, R², R³, R⁴ and X have the same meanings as in formula I, with compounds containing phosphorus-hydrogen bonds corresponding to the general formula

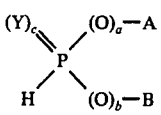

in which a, b, c and Y have the same meanings as in formula I and in which A represents an alkyl radical or, where $a = 0$, also an aryl radical, and B represents an alkyl radical or, where $b = 0$, also an aryl radical, in the presence of known radical initiators or high-energy radiation at temperatures of from about 50° to about 300° C, and optionally hydrolyzing the resulting reaction products. Examples are:

1-methyl-1-oxophospholane phosphonic acid,
1-methyl-1-oxophospholane phosphonic acid monomethyl ester,
1-methyl-1-oxophospholane phosphonic acid monoethyl ester,
1-methyl-1-oxophospholane phosphonic acid monobutyl ester, the monosodium salt of 1-methyl-1-oxophospholane phosphonic acid, the disodium salt of 1-methyl-1-oxophospholane phosphonic acid, the monotriethyl ammonium salt of 1-methyl-1-oxophospholane phosphonic acid,
1-methyl-1-oxophospholanyl methyl phosphinic acid,
1-methyl-1-oxophospholanyl ethyl phosphinic acid,
1-methyl-1-oxophospholanyl phethyl phosphinic acid,
1-ethyl-1-oxophospholane phosphonic acid,
1-phenyl-1-oxophospholane phosphonic acid,
1-methyl-1-thiophospholane phosphonic acid,
1-methyl-1-oxophospholane thiophosphonic acid,
1,3-dimethyl-1-oxophospholane phosphonic acid, also their salts, especially their alkali metal and ammonium salts, and mixtures of the above-mentioned acids with their salts. Other phospholane phosphonic acid monoalkyl esters which cannot be obtained by the above-mentioned process may be obtained for example by esterifying the corresponding phospholane phosphonic acid by conventional methods, for example by reaction with orthocarboxylic acid esters or orthocarbonic acid esters or trialkylphosphites.

The following are mentioned as examples of the alkylene oxides and alkylene imines of the general formula (V) used in the method according to the invention, which are also known in large numbers (cf. Houben Weyl, Methoden der organischen Chemie, Vol. VI, 3, pages 367 et seq): propylene oxide, ethylene oxide, α-epichlorhydrin, α-epibromhydrin, 1,2-butylene oxide, 2,3-butylene oxide, isobutylene oxide, cyclohexene oxide, 3,4-epoxy-1-butene, butadiene dioxide, styrene oxide, 9,10-epoxy stearic acid, 2,3-epoxy-4-oxo-2-methyl pentane, glycide, glycide acetate and other carboxylic acid glycide esters, glycidyl methacrylate, glycidyl propionitrile, glycidyl vinyl ether, glycidyl methyl ether, glycidyl allyl ether, glycidyl phenyl ether, diglycidyl ether, glycidyl phenyl urethane, tolylene diglycidyl urethane, triglycidyl cyanurate, glycidyloxy silanes, triglycidyl phosphate, triglycidyl phosphite, 3-glycidopropyl trimethoxy silane, ethylene imine, propylene imine, isobutylene imine, butylene imine, n-octyl aziridine, 2-hydroxy ethyl aziridine, 2-aminoethyl aziridine, 3-aminopropyl aziridine, cyclohexyl aziridine, 2-methoxy ethyl aziridine, 2-carboethoxy ethyl aziridine.

It is also possible to react mixtures of different alkylene oxides and alkylene imines of general formula V with the above mentioned phospholane phosphonic acids and the phospholane phosphinic acids of general formula III or their salts. It is also possible initially to react the phospholane phosphonic acid or phospholane phosphinic acid with one or more alkylene oxides and/or alkylene imines and further to react the product obtained therefrom either once or more times with one or more other alkylene oxides and/or alkylene imines.

A total of about 0.1 to 30 moles of alkylene oxide and/or alkylene imine per 1 g-equivalent of acid is used for the reaction by which the compounds according to the invention are formed. In cases where less than 1 mole of alkylene oxide and/or alkylene imine is used per g-equivalent of acid, the products according to the invention are obtained in solution in the starting material. Products still containing acidic groups may be neutralized in known manner, for example with monomeric and polymeric amines and other nitrogen-containing bases, with phosphines, ammonium, phosphonium or arsonium hydroxides, ammonium or phosphonium salts of weak acids with $pK_s >$ about 2, with metal oxides, metal hydroxides, metal salts of weak acids with $pK_s > 2$ and by reaction with base metals and by so-called double reaction with metal salts or with monomeric or polymeric ammonium or phosphonium salts or the salts of other nitrogen-containing bases, or may be converted into the corresponding esters, again in known manner, for example with orthocarboxylic acid esters or with other known alkylating agents. In the event of complete alkylation, unreacted alkylene oxide and/or alkylene imine is best removed by vacuum distillation on completion of the reaction. The reaction by which the compounds according to the invention are formed is carried out at temperatures of about 0° to about 180° C and preferably at temperatures of about 50° to 150° C.

Although it is not absolutely essential for the reaction according to the invention to be carried out in the presence of a solvent, a solvent may be particularly useful in cases where the phospholane phosphonic acid or phospholane phosphinic acid to be reacted is solid or extremely viscous at the reaction temperature. Suitable solvents are, for example, alcohols, glycols and polyols, chlorinated hydrocarbons, ethers, water, dioxane, alkanolamines, carboxylic acid esters, ketones, nitriles, amines, amides, phosphinoxides, phosphoric acid esters, phosphonic acid esters, phosphoric acid amides, but preferably the reaction products of formula I themselves. Both alkylene oxide and/or alkylene imine and also the phospholane phosphonic acids and phospholane phosphinic acids may be dissolved in the solvent and reacted as such.

In cases where the reaction according to the invention is carried out with the salts of the phospholane phosphonic or phospholane phosphinic acids in aqueous medium, the base formed during the reaction has to be constantly neutralized.

Solvents containing free O—H— and/or N—H— groups are also oxalkylated and/or aminoalkylated during the reaction. It is particularly advisable to use solvents containing O—H— or N—H—groups in cases where subsequent reactions require the presence of reactants containing O—H— or N—H groups.

In cases where a phospholane phosphonic acid can only be reacted with alkylene oxides and/or alkylene imines of formula V in the presence of a solvent, for example as a result of excessive viscosity at the reaction temperature, it is possible to obtain solvent-free products by initially carrying out the reaction with a mixture of phospholane phosphonic acid or phospholane phosphinic acid and the necessary quantity of solvent and using the reaction product as medium for dissolving the phospholane phosphonic acid or phospholane phosphinic acid to be reacted in the following batch.

In cases where this principle is repeatedly applied, the solvent used becomes increasingly dilute and the products obtained are substantially free from the solvent added to the first batch and its oxalkylation and/or aminoalkylation products. The same result is obtained by initially reacting a little phospholane phosphonic acid or phosphinic acid in the necessary quantity of solvent with alkylene oxide and/or alkylene imine and then introducing phospholane phosphonic acid or phospholane phosphinic acid and alkylene oxide and/or alkylene imine either continuously or in portions. The solvent becomes increasingly dilute. Products with even smaller residual contents of solvents are obtained when the product, which only contains very dilute solvent, is used as a medium for dissolving the phospholane phosphonic acid or phospholane phosphinic acid in the next batch. It is also possible to remove product from a batch started in the manner described with a little phospholane phosphonic acid or phospholane phosphinic acid and the appropriate quantity of solvent either continuously or in portions, according to whether fresh reactants are added continuously or in portions. After a startup phase, solvent-free product is obtained.

In general, the reaction is carried out by adding liquid or gaseous alkylene oxide and/or alkylene imine to the phospholane phosphonic acid or phospholane phosphinic acid, although the reactants may also be added in the reverse order given suitable conditions which completely prevent the alkylene oxide and/or alkylene imine from escaping from the reaction vessel. It is also possible in accordance with the invention to introduce the reactants simultaneously into the reaction vessel so that the process may also be carried out continuously. The reaction is best carried out with thorough mechanical stirring of the reactants. The process according to the invention may be carried out either under normal pressure and at elevated pressure. Although it is not normally advantageous to apply reduced pressure on account of the volatility of the alkylene oxides and/or alkylene imines and the resulting deceleration of the reaction, it is nevertheless also possible in principle to carry out the reaction at reduced pressure, especially in cases where such a procedure is necessary for safety reasons. The atmosphere over the reaction mixture may consist of air or preferably of an inert gas for example, nitrogen, or even of the alkylene oxides and/or alkylene imines to be reacted.

In general, no further catalysts are required for carrying out the reaction according to the invention, although it is possible to use acid and basic catalysts known per se, such as mineral acids, metal chlorides, non-metal chlorides, alkali hydroxides, alkali carbonates and amines. Catalysts have to be added particularly in cases where it is desired further to extend the 2-hydroxy alkyl radical or 2-aminoalkyl radical formed with more alkylene oxide and/or alkylene imine beyond esterification of the phospholane phosphonic acids and phosphinic acids.

It is also possible in accordance with the invention partially to react the phospholane phosphonic acids or phospholane phosphinic acids with alkylene oxides and/or alkylene imines in the absence of a catalyst and to continue oxalkylation and/or aminoalkylation in the presence of a catalyst with the same or different alkylene oxides and/or alkylene imines or mixtures thereof.

The products according to the invention have very interesting properties which derive from the simultaneous presence of the phospholane oxide structure and one or two reactive O—H— and/or N—H—groups and also from the high phosphorus content. By varying the starting materials, it is thus possible to obtain products with specific hydrophilic/lipophilic ratios. By virtue of the presence in them of terminal hydroxyl and/or amino groups, they are suitable for use as reactants in the production of polyesters, polyamides, polycarbonates and polyurethanes.

Accordingly, the compounds according to the invention represent valuable products and starting materials, for example for the plastics, lacquer and textile sectors where they show antistatic, surface-active and fire-retarding characteristics.

In addition, they are suitable for converting isocyanates into carbodiimides in accordance with the disclosure of application Ser. No. 648,710, referred to hereinabove. By comparison with conventional systems, they surprisingly have the advantage that, to obtain a sufficiently long cream time in the production of a foam with a polycarbodiimide structure, there is no need for the addition of further catalysts of the kind described in German DOS No. 2,245,634.

In particular, their terminal hydroxyl groups and/or amino groups enable them to be incorporated in prepolymers and polymers which are thus given the catalytic activity referred to above for converting isocyanates into carbodiimides. In addition, they represent flameproofing agents suitable for incorporation in synthetic organic plastics.

The invention is illustrated by the following Examples.

EXAMPLE 1

In a stirrer-equipped flask, 50 g of 1-methyl oxophospholane phosphonic acid were dissolved in 25 g of ethylene glycol. A total of 81 g of propylene oxide was added dropwise below the surface of the mixture over a period of 1 hour at 100° to 110° C. Thereafter, no more propylene oxide was consumed and the excess propylene oxide boiled under reflux. After 1 hour, the excess propylene oxide was removed in vacuo. The total weight then amounted to 154 g, corresponding to an uptake of 79 g of propylene oxide.

Determination of the acid content in cold aqueous solution showed that no more phospholane phosphonic acid was present. Accordingly the solution consisted of 38.5 mole % of

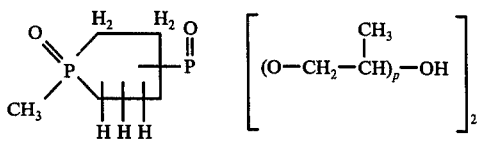

and of 61.5 mole % of

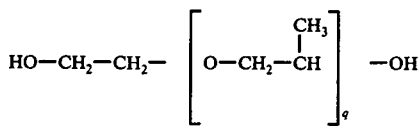

where $p + q = 2.7$.

The reaction of 50 g of 1-methyl-1-oxophospholane phosphonic acid with excess propylene oxide was repeated another six times with 25 g of the reaction product of each preceding batch as solvent instead of the ethylene glycol used in the first batch, and it was found that the product of the sixth batch had the following composition:

53.8% C — 9.0% H — 6.1% P, which corresponds to the formula

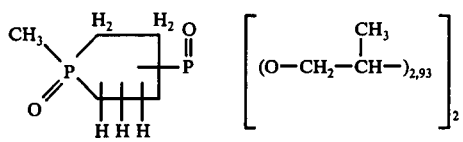

Theoretically the impurity content attributable to ethylene glycol had fallen to less than 5 mole %.

In the following Examples 2 to 12, the compounds according to the invention can be similarly obtained in substantially pure form.

EXAMPLE 2

50 g of 1-methyl-1-oxophospholane phosphonic acid were dissolved in a mixture of 25 g of ethylene glycol and 2.5 g of trimethylol propane and the resulting solution was reacted with propylene oxide in the manner described in Example 1 until there was no further uptake of propylene oxide. Removal of the unused propylene oxide left behind 158 g of residue which no longer had any acid properties in aqueous solution.

EXAMPLE 3

50 g of 1-methyl-1-oxophospholane phosponic acid were mixed with 25 g of ethylene glycol in a stirrer-equipped flask. 58 g of propylene oxide were added dropwise below the surface of the mixture over a period of 30 minutes at 100° - 110° C. After reaction for one hour at this temperature, the flask was evacuated. Thereafter the total weight amounted to 133 g, i.e. the uptake of propylene oxide was quantitative. Titration of a sample in aqueous solution showed that the total of 65 millimoles of 1-methyl-1-oxophospholane phosphonic acid and 48 millimoles of 1-methyl-1-oxophospholane phosphonic acid mono-(poly)-propylene glycol ester were present in addition to 139 millimoles of 1-methyl-1-oxophospholane phosphonic acid-bis-(poly)-propylene glycol ester.

EXAMPLE 4

58 g of propylene oxide were added dropwise at 70° C to, and below the surface of, a mixture of 50 g of 1-methyl-1-oxophospholane phosphonic acid, 25 g of ethylene glycol and 1 g of pyridine. The initially hazy mixture clarified during the reaction. Titration of a sample in aqueous solution showed that 72 millimoles of 1-methyl-1-oxophospholane phosphonic acid mono-(poly)-propylene glycol ester were present in addition to 12.5 millimoles of its pyridinium salt and 168 millimoles of 1-methyl-1-oxophospholane phosphonic acid-bis-(poly)-propylene glycol ester.

EXAMPLE 5

10 g of propylene oxide were added dropwise at 100° - 110° C to 67 g of the product of Example 4. Thereafter no more propylene oxide was taken up. Following the removal of excess propylene oxide, titration in aqueous solution showed that no more acid was present in the product.

EXAMPLE 6

50 g of 1-methyl-1-oxophospholanyl methyl phosphinic acid and 0.3 ml of boron trifluoride etherate were made into a paste with 25 g of propylene glycol, followed by the dropwise addition of propylene oxide at 100° - 110° C. After 26 g of propylene oxide had been added, vigorous refluxing of propylene oxide took place in the reflux condenser. The mixture was left reacting for 30 minutes. Excess propylene oxide was removed in vacuo. The residue, which was shown by titration in aqueous medium to be free of acid, weighed 100 g. The following composition was attributed to it: 0.275 mole of

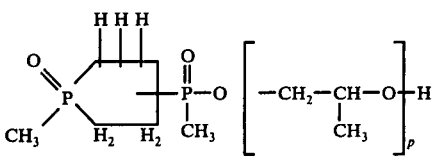

and 0.329 mole of

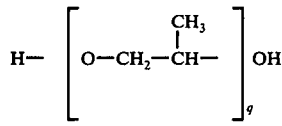

where $p + q = 1.54$.

EXAMPLE 7

A total of 100 g of propylene oxide was added dropwise at 70° C to 50 g of 1-methyl-1-oxophospholane phosphonic acid monomethyl ester. After 8 hours, unused propylene oxide was removed in vacuo. The residue weighed 68 g. The titration of a sample in aqueous solution showed that there had been an 83% conversion into 1-methyl-1-oxophospholane phosphonic acid monomethyl mono-(poly)-propylene glycol ester.

EXAMPLE 8

15 g of epichlorhydrin were added dropwise over a period of 1 hour at 80 to 90° C to 66 g of the product of Example 4. After 3 hours, unreacted epichlorhydrin was removed in vacuo. The residue weighed 72 g. No more acid was present.

EXAMPLE 9

50 g of phospholane phosphonic acid were mixed at 20° C with 25 g of diethylene glycol, followed by the dropwise addition at that temperature of 44 g of ethylene oxide. The ethylene oxide was introduced below the surface of the mixture. It was not taken up completely. Evacuation left 90 g of residue in which approximately 60% of the 1-methyl-1-oxophospholane phosphonic acid used was still present, whereas 4.5% had been converted into a monoester and 36% into a diester.

EXAMPLE 10

110 g of epichlorhydrin were added dropwise at 90° C to a solution of 50 g of phospholane phosphonic acid in 25 ml of ethylene glycol. After 2 hours, unreacted epichlorhydrin was removed from the reaction mixture in vacuo. The residue left weighed 151 g and contained less than 0.015 mg equivalent of acid/g of substance.

EXAMPLE 11

50 g of 1-methyl-1-oxophospholane phosphonic acid were mixed with 25 g of ethylene glycol, followed by the dropwise addition at 90° C of 114 g of glycidyl allyl ether. On completion of the addition, the mixture was kept for 1 hour at 90° C. Thereafer readily volatile fractions were removed in vacuo. The residue weighed 187 g, so that the uptake of glycidyl allyl ether amounted to 112 g. 89.5% of the 1-methyl-1-oxophospholane phosphonic acid used had been converted into a diester and 10.5% into a monoester.

EXAMPLE 12

51 g of 1-methyl-1-oxophospholane phosphonic acid mono-i-butyl ester together with 40 g of trimethyl phosphate were introduced into a stirrer-equipped flask. 40 g of propylene oxide were added in small portions at 90° C. After 2 hours, solvent and unused propylene oxide were removed in vacuo. The residue weighed 78 g. According to titration, 96% of the acid used was present as diester and 4% as monoester.

EXAMPLE 13

9.8 Parts by weight of maleic acid anhydride and 5.2 parts by weight of diethylene glycol were heated to 175° C with 25.6 parts by weight of a diester of an isomeric mixture of 1-methyl-2- and 3-phosphoric acid phospholane oxide and polypropylene glycol (molecular weight 511) under an atmosphere of nitrogen, and the water formed in the esterification reaction was distilled off. The gel-like product was mixed with 0.6 parts by weight of benzoyl peroxide and heated to 150° C. Soluble components were removed from the resulting crumbly product by extraction with toluene and chloroform.

When 1 part by weight of the catalyst was heated to 110° C with 34.8 parts by weight of a mixture of 2,4- and 2,6-tolylene diisocyanate (80:20), 2 liters of carbon dioxide were evolved over a period of 10 minutes.

It will be appreciated that the instant specification and examples are set forth by way of illustration and not limitation, and that various modifications and changes may be made without departing from the spirit and scope of the present invention.

What is claimed is:

1. A hydroxyalkyl or aminoalkyl ester of a phospholane phosphonic or phosphinic acid of the formula

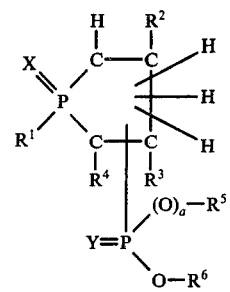

in which $a$ is 0 or 1, $R^1$ is alkyl with 1 to 10 carbon atoms or aryl with up to 14 carbon atoms, $R^2$, $R^3$ and $R^4$ each independently is alkyl with 1 to 4 carbon atoms, hydrogen, chlorine or bromine, $R^5$ is alkyl with 1 to 8 carbon atoms and, where $a = 0$, optionally an aryl radical with up to 8 carbon atoms and, where $a = 1$, also optionally 1/m of an m-valent cation or a hydroxy alkylene or imino alkylene radical of the formula

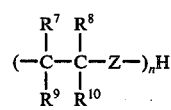

$R^6$ is a hydroxy alkylene or imino alkylene radical of the formula

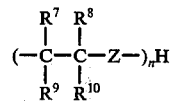

$R^7$ and $R^8$ each independently is hydrogen, alkyl with 1 to 6 carbon atoms, phenyl, alkenyl with 2 to 4 carbon atoms, chloromethyl, bromomethyl, hydroxy methyl or etherified or esterified hydroxy methyl, in addition to which $R^7$ and $R^8$ may together be an alkylene bridge of 2 to 4 carbon atoms to form a ring, $R^9$ and $R^{10}$ each independently is hydrogen or alkyl with 1 to 2 carbon atoms, Z is oxygen or imino, $n$ is a number from 1 to 30, and X and Y each independently is oxygen or sulphur.

2. An ester according to claim 1 wherein $a = 1$ and $R^5$ is selected from the group consisting of an alkali metal, ammonium, guanidinium, phosphonium and hydrogen cation.